(12) United States Patent
Ong et al.

(10) Patent No.: US 11,800,975 B2
(45) Date of Patent: Oct. 31, 2023

(54) EYE FATIGUE PREDICTION BASED ON CALCULATED BLOOD VESSEL DENSITY SCORE

(71) Applicant: Intel Corporation, Santa Clara, CA (US)

(72) Inventors: Sheow Ong, Simpang Ampat (MY); Wei Yuan Kong, Perai (MY); Kar Mun Tham, Bayan Lepas (MY)

(73) Assignee: Intel Corporation, Santa Clara, CA (US)

( * ) Notice: Subject to any disclaimer, the term of this patent is extended or adjusted under 35 U.S.C. 154(b) by 548 days.

(21) Appl. No.: 16/989,246

(22) Filed: Aug. 10, 2020

(65) Prior Publication Data

US 2021/0022604 A1     Jan. 28, 2021

Related U.S. Application Data

(63) Continuation of application No. 16/005,828, filed on Jun. 12, 2018, now Pat. No. 10,736,505.

(51) Int. Cl.

| | |
|---|---|
| *A61B 3/113* | (2006.01) |
| *A61B 3/10* | (2006.01) |
| *G06V 40/18* | (2022.01) |
| *G06V 40/16* | (2022.01) |
| *A61H 5/00* | (2006.01) |
| *G06V 40/14* | (2022.01) |

(52) U.S. Cl.
CPC .............. *A61B 3/113* (2013.01); *A61B 3/10* (2013.01); *G06V 40/161* (2022.01); *G06V 40/18* (2022.01); *G06V 40/193* (2022.01); *A61H 5/00* (2013.01); *G06V 40/14* (2022.01)

(58) Field of Classification Search
CPC ........ A61B 3/113; A61B 3/10; G06V 40/161; G06V 40/18; G06V 40/193; G06V 40/14; A61H 5/00
USPC .......................................... 351/200, 205, 206
See application file for complete search history.

(56) References Cited

U.S. PATENT DOCUMENTS

| | | | |
|---|---|---|---|
| 10,736,505 B2 | 8/2020 | Ong et al. | |
| 2014/0180162 A1 | 6/2014 | Schuhrke et al. | |
| 2017/0112377 A1 | 4/2017 | Shiba et al. | |
| 2023/0004008 A1* | 1/2023 | Samec | A61B 5/369 |

OTHER PUBLICATIONS

United States Patent and Trademark Office, "Non-Final Office Action," issued in connection with U.S. Appl. No. 16/005,828, dated Nov. 26, 2019, 8 pages.
United States Patent and Trademark Office, "Notice of Allowance and Fee(s) Due," issued in connection with U.S. Appl. No. 16/005,828, dated Apr. 6, 2020, 9 pages.

* cited by examiner

*Primary Examiner* — Tuyen Tra
(74) *Attorney, Agent, or Firm* — Hanley, Flight & Zimmerman, LLC

(57) ABSTRACT

An example apparatus for predicting eye fatigue includes an image receiver to receive an image of an eye. The apparatus also includes a fatigue predictor to predict eye fatigue in the eye based on a calculated blood vessel density score of the eye in the image. The apparatus further includes an alert generator to generate an alert in response to predicting the eye fatigue.

16 Claims, 8 Drawing Sheets

402

1

EYE FATIGUE PREDICTION BASED ON CALCULATED BLOOD VESSEL DENSITY SCORE

RELATED APPLICATION

This patent is a continuation of U.S. patent application Ser. No. 16/005,828, filed on Jun. 12, 2018 (now U.S. Pat. No. 10,736,505). Priority is claimed to U.S. patent application Ser. No. 16/005,828. U.S. patent application Ser. No. 16/005,828 is hereby incorporated by reference in its entirety.

BACKGROUND

Virtual reality (VR) systems may be used to simulate realistic visual experiences. For example, VR systems may enable users to experience a fully immersed experience in a virtual reality world.

BRIEF DESCRIPTION OF THE DRAWINGS

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

Figure 1:
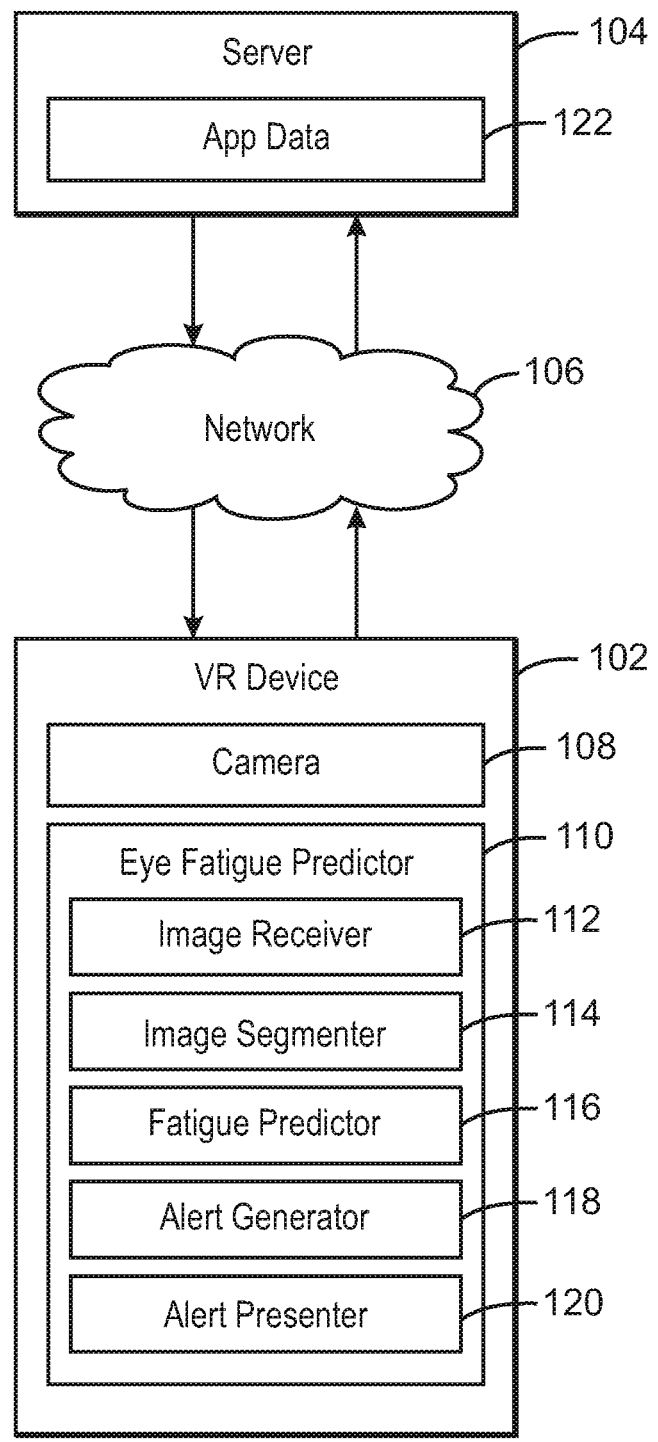
FIG. 1 is a block diagram illustrating an example system for predicting eye fatigue.

As discussed above, VR systems may enable users to experience a fully immersed experience in a virtual reality world. For example, users may spend hours exploring virtual reality worlds in the comfort of their homes. However, users may not notice computer vision syndrome (CVS) that may be caused by the long hours of usage. As used herein, CVS refers to a condition resulting from focusing the eyes on a computer or other display device for protracted, uninterrupted periods of time, and the eye muscles being unable to recover from the strain due to a lack of adequate rest, including any associated symptoms. For example, symptoms of CVS may include headaches, blurred vision, neck pain, fatigue, eye strain, dry eyes, irritated eyes, double vision, vertigo/dizziness, polyopia, and difficulty refocusing the eyes. Even if users are aware of measures for preventing symptoms of CVS, users may forget about such techniques while focusing on activities such as a VR game. For example, such preventative measures may include a "20-20-20" rule where a user may look at an object 20 feet away for 20 seconds every 20 minutes of using a VR headset, among other techniques. In addition, different environments may contribute to varying degrees of CVS. For example, the dryness of a room and the brightness of a VR device may be among other factors that may contribute to varying amounts of eye fatigue associated with CVS.

The present disclosure relates generally to techniques for predicting eye fatigue. Specifically, the techniques described herein include an apparatus, method and system for predicting eye fatigue based on a calculated blood vessel density score. As used herein, blood vessel density refers to the proportion of a sclera of an eye that contains blood vessels. For example, the eye fatigue may be caused by prolonged use of VR systems. In some examples, the eye fatigue may be predicted based on a calculated blood vessel density score in the sclera of the eye in captured images. The sclera, also known as the white of the eye, is the opaque, fibrous, protective, outer layer of the eye containing mainly collagen and some elastic fiber. In humans, the whole sclera may be white, contrasting with the colored iris. An example apparatus includes an image receiver to receive an image of an eye. The apparatus includes a fatigue predictor to predict eye fatigue in the eye based on a calculated blood vessel density score of the eye in the image. The apparatus further includes an alert generator to generate an alert in response to predicting the eye fatigue.

The techniques described herein thus increase awareness of eye fatigue during VR system use. For example, the users may be alerted to eye strain as it is occurring and take ameliorative actions to prevent computer vision syndrome. In particular, users may take a break or perform some exercise to reduce eye strain. Moreover, the techniques may provide reduced physical discomforts caused by headaches, neck aches, and back aches. For example, the techniques described herein may be used to indicate appropriate times for a user to stretch or perform some other exercise to reduce or prevent such aches. The techniques may thus also be used to reduce the risk of presbyopia in the long term. Presbyopia refers to the reduction of flexibility of the eyes in focusing on near and far objects with age.

FIG. 1 is a block diagram illustrating an example system for predicting eye fatigue. The example system is referred to generally by the reference number 100 and can be implemented in the computing device 700 below in FIG. 7 using the method 600 of FIG. 6 below.

The example system 100 includes a VR device communicatively coupled to a server 104 via a network 106. For example, the server 104 may be a node of a cloud computing network. The VR device includes a camera 108. For example, the camera 108 can capture images of the eyes of a user of the VR device 102. The VR device 102 further includes an eye fatigue predictor 110 to predict eye fatigue during the use of the VR device 102. The eye fatigue predictor 110 includes an image receiver 112 communicatively coupled to the camera 108 to receive images from the camera 108. The eye fatigue predictor 110 further includes an image segmenter 114 to segment received images into sclera regions and extract the sclera regions. The eye fatigue predictor 110 includes a fatigue predictor 116 that can predict eye fatigue based on an analysis of extracted sclera regions. The eye fatigue predictor 110 includes an alert generator 118 to generate an alert in response to predicting eye fatigue. The eye fatigue predictor 110 includes an alert presenter 120 to present the alert to a user of the VR device 102. Each component, such as the eye fatigue predictor 110, the image segmenter 114, fatigue predictor 116, alert generator 118, and alert presenter 120 may be implemented via a configurable circuit, such as a field programmable gate array.

As shown in FIG. 1, a user is using or operating the VR device 102. For example, the user may be playing a VR video game or using a VR application. While the user is using the VR device 102, the VR device 102 may collect images of the eyes of the user via the camera 108. The image receiver 112 may receive the captured images from the camera 108. The image segmenter 114 may then segment the images into sclera and background regions. For example, the image segmenter 114 may segment the images based on curve lines of the eyelid and the iris of each eye. The fatigue predictor 116 may then analyze the blood vessel density in the extracted sclera regions of the eyes. In some examples, the processor may also extract one or more sampling images from the extracted sclera region. The fatigue predictor 110 calculates a blood vessel density for each of the sampling images of the eyes and find an average score for all of the sampling images. For example, the fatigue predictor 110 may calculate a blood vessel density score using the equation:

$$f(n) = \frac{\left(\frac{\sum_{i=1}^{n}(\alpha)}{n}\right) - \beta}{\beta} \qquad \text{Eq. 1}$$

where α is the blood vessel density in a sampled sclera region, β is the preset baseline score for a user, and n is the number of samples of different sclera regions in a detected sclera of an eye. For example, the blood vessel density may be the blood vessel pixel density or ratio of blood vessel pixels over the total pixels in a sampled sclera region. In some examples, the blood vessel density α may be calculated using any suitable computer vision function. In some examples, an initial β baseline score may be calculated using the f(n) score during profile creation during a first use. Then the value of baseline score β may be adjusted automatically based on a lowest f(n) score over time. For example, the blood vessel density may be calculated based on an area of the blood vessels as compared to the total area of a sclera region. In some examples, the fatigue predictor 116 may detect an amount of blood vessel density in an extracted sclera region exceeds a predefined threshold amount of blood vessel density. In some examples, the threshold may be based on a preset baseline density for a user and a preset difference from the baseline density. For example, the threshold score may be a predetermined amount of density higher than a preset baseline density score.

As one example of the eye fatigue prediction, a user may turn on the eye fatigue prediction feature and start a gaming session. The feature may have a pre-set threshold at 75% and baseline score β of 0.01. At 0 hours, blood vessel density α is capture as 0.01. Using these values in Eq. 1 above gives:

$$\int_{1}^{n} = \frac{\sum_{1}^{n}(0.01 + \ldots \ln) - 0.01}{0.01} = 0.05 \qquad \text{Eq. 2}$$

a resulting average blood density score of 0.05 may be calculated. As 0.05 less than the threshold of 0.75, there would be no alert generated during this time. At the end of the first hour, a blood vessel density α may be calculated as 0.015. Again, using these values in Eq. 1 above gives:

$$\int_{1}^{n} = \frac{\sum_{1}^{n}(0.015 + \ldots \ln) - 0.01}{0.01} = 0.05 \qquad \text{Eq. 3}$$

a resulting average blood density score of 0.5. As 0.5 is still less 0.75, there would also be no alert generated during at the first hour. At the end of a second hour, the blood vessel density α is calculated as 0.02. Using Eq. 1 with this value gives:

$$\int_{1}^{n} = \frac{\sum_{1}^{n}(0.02 + \ldots \ln) - 0.01}{0.01} = 1. \qquad \text{Eq. 4}$$

a resulting average blood density score of 1. As 1 is more than the threshold 0.75, an eye fatigue may be predicted, and the alert may be triggered and be sent to the user.

In response to detecting a predicted eye fatigue, the alert generator 118 may generate an alert. For example, the alert may be a visual alert, an audible alert, or both. The alert presenter 120 may present the alert to a user. For example, the alert presenter 120 may display a visual alert to a user via a display of the VR device 102 or play an audible alert via a speaker of the VR device 102, or both.

The VR device 102 may also collect current user profile data, application configuration data, and upload the user profile and application configuration and usage data to the server 104. In some examples, the server 104 may be a node in a cloud storage solution.

The application (app) data 122 may thus include saved user profiles and configurations. The app data 122 may also include app usage history. For example, the app data 122 may include previously used blood vessel density baselines and thresholds associated with a particular user. Thus, when a user logs into an application using a particular user account, then the baseline blood vessel density and threshold may automatically be loaded for use in predicting eye fatigue.

The diagram of FIG. 1 is not intended to indicate that the example system 100 is to include all of the components shown in FIG. 1. Rather, the example system 100 can be implemented using fewer or additional components not illustrated in FIG. 1 (e.g., additional cameras, eye fatigue predictors, VR devices, networks, servers, etc.).

Figure 2:
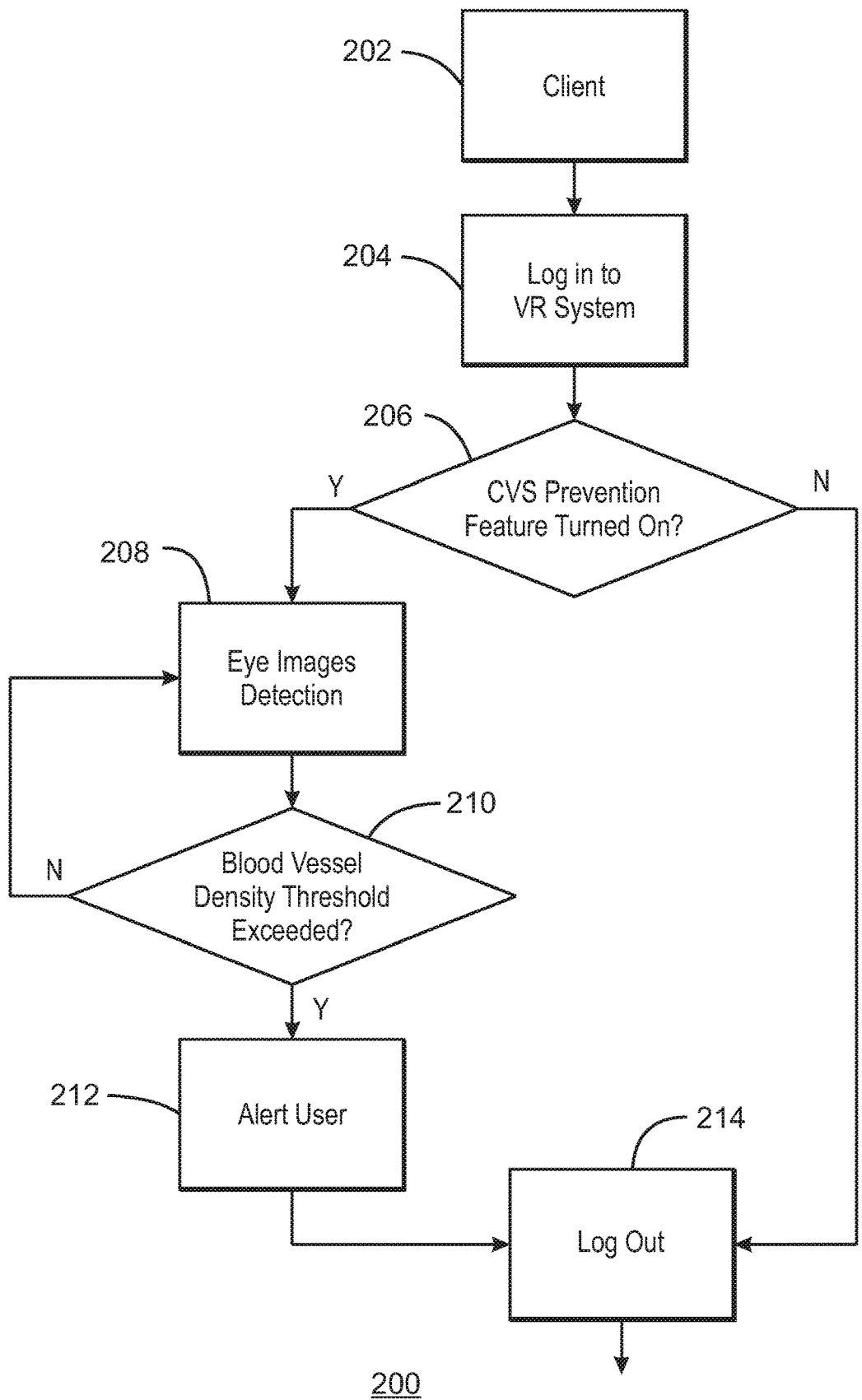
FIG. 2 is a schematic diagram illustrating an example method for alerting users of predicted eye fatigue.

FIG. 2 is a schematic diagram illustrating an example method for alerting users of predicted eye fatigue. The example process is generally referred to by the reference number 200 and can be implemented in the system 100 above or the computing device 700 below.

In the example method 200, a client 202 may log in to a VR system at block 204. For example, the client may log in to the VR system using a selected profile including one or more settings. The profile may include a baseline density score and a previously used blood vessel density threshold for eye fatigue prediction. At decision diamond 206, a processor may determine whether a computer vision syndrome (CVS) prevention feature is turned on. For example, the CVS prevention feature may be the fatigue predictor, alert generator and alert presenter described above in FIG. 1. If the CVS prevention feature is turned on, then the method may proceed at block 208. If the CVS prevention feature is turned off, then the method may proceed at block 214 as described below.

At block 208, the processor detects one or more eye images. For example, the processor may receive the one or more eye images from a camera or other imaging device in the VR system. The processor may segment the one or more eye images and extract a sclera region from each of the one or more eye images. In some examples, the processor may also extract one or more sampling images from the extracted sclera region. The processor may further calculate a blood vessel density score for each of the sampling images. For example, the blood vessel density score may be calculated and averaged as described using Eq. 1 of FIG. 1 above.

At decision diamond 210, the processor determines whether a blood vessel density score threshold is exceeded. For example, the processor may compare a calculated average blood vessel density score to the threshold. If the blood vessel density score threshold is exceeded, then the method may continue at 212. If the blood vessel density score threshold is not exceeded, then the method may continue back to block 208 above.

At block 212, the processor alerts a user of a predicted eye fatigue. For example, the processor may generate a sound, visual display, or haptic feedback to alert the user of the predicted eye fatigue and present the alert to the user.

At block 214, the client logs out of the VR system. The processor may receive input from the client to log out. The processor may stop receiving and analyzing additional eye images.

This process flow diagram is not intended to indicate that the blocks of the example process 200 are to be executed in any particular order, or that all of the blocks are to be included in every case. Further, any number of additional blocks not shown may be included within the example process 200, depending on the details of the specific implementation.

Figure 3:
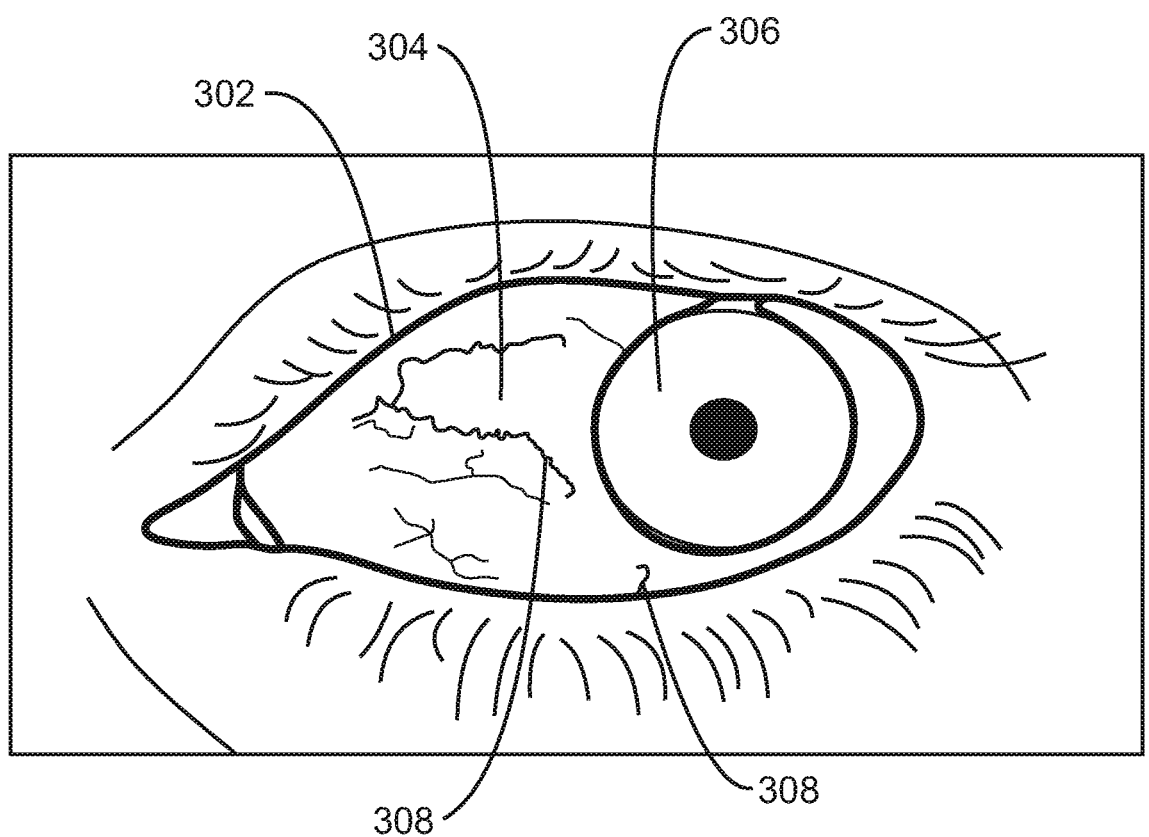
FIG. 3 is a diagram illustrating an example image of an eye displaying symptoms of eye fatigue.

FIG. 3 is a diagram illustrating an example image of an eye displaying symptoms of eye fatigue. The example image is generally referred to by the reference number 300 and can be implemented in the computing device 700 below. For example, the image 300 can be generated using the camera 108 of the system 100 of FIG. 1, the camera 726 of the computing device 700 of FIG. 7 below, and used by the image receiver 806 of the computer readable media 800 of FIG. 8 below.

FIG. 3 shows an eye 302 including a sclera 304 and an iris 306. The sclera includes visible blood vessels 308. In some examples, the sclera region 304 of the eye 302 may be extracted with the blood vessels 308 using the techniques described herein. For example, the sclera region 304 may be segmented from a background region and extracted using curvature lines of the eyelid and the iris 306. An example segmented and extracted sclera region 304 is shown in FIG. 4 below.

The diagram of FIG. 3 is not intended to indicate that the example image 300 is to include all of the components shown in FIG. 3. Rather, the example image 300 can be implemented using fewer or additional components not illustrated in FIG. 3 (e.g., additional eyes, sclera, blood vessels, etc.).

Figure 4:
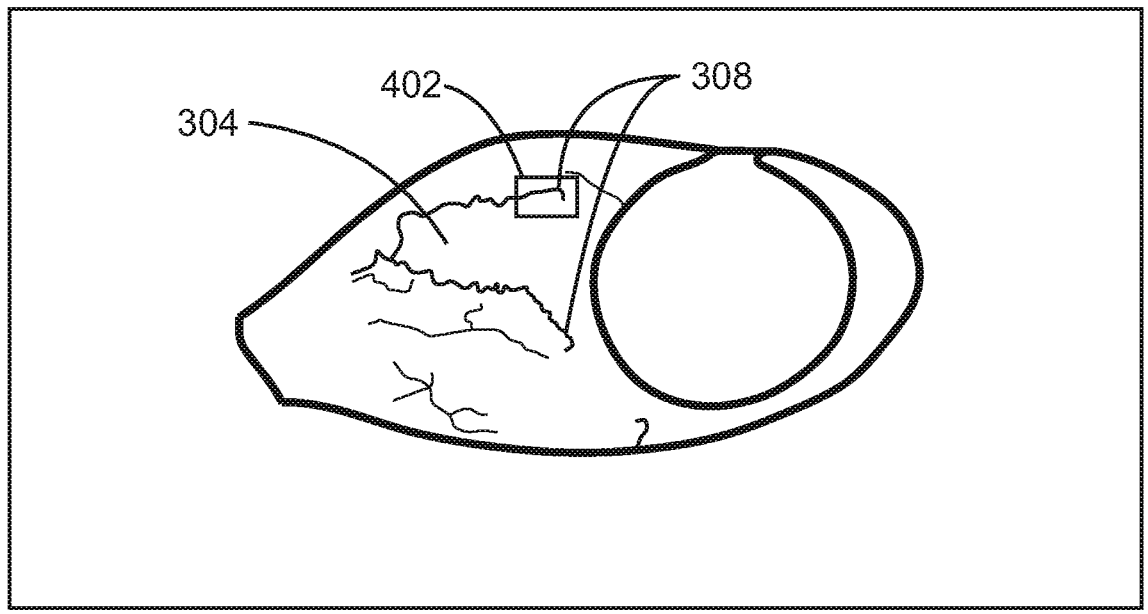
FIG. 4 is a diagram illustrating an example extracted sclera region of an image of an eye displaying symptoms of eye fatigue.

FIG. 4 is a diagram illustrating an example extracted sclera region of an image of an eye displaying symptoms of eye fatigue. The example extracted sclera region is generally referred to by the reference number 400 and can be implemented in the computing device 700 below. For example, the extracted sclera region 400 can be generated using the image segmenter 114 of the system 100 of FIG. 1, the image segmenter 732 of the computing device 700 of FIG. 7 below, or using the image segmenter module 808 of the computer readable media 800 of FIG. 8 below.

FIG. 4 shows an extracted sclera region 304 including a number of blood vessels 308. The example extracted sclera region 402 also includes a sampling image 402 region. For example, the extracted sclera region 402 may be sent to an eye fatigue predictor that can analyze the sclera region 402 for eye fatigue based on blood vessel density. In some examples, one or more sampling images 402 may be extracted from the sclera region 304. The extracted sampling images 402 may be used to calculate a blood vessel density score as described above. An example close-up of the extracted sampling image 402 is shown and described in greater detail with respect to FIG. 5 below.

The diagram of FIG. 4 is not intended to indicate that the example extracted sclera region 400 is to include all of the components shown in FIG. 4. Rather, the example extracted sclera region 400 can be implemented using fewer or additional components not illustrated in FIG. 4 (e.g., additional eyes, sclera, blood vessels, etc.).

Figure 5:
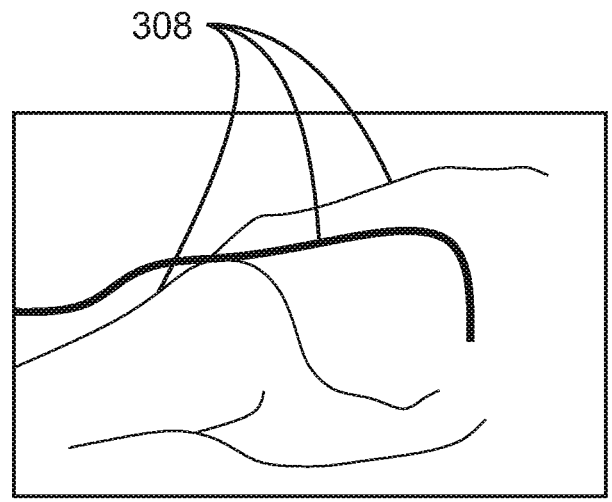
FIG. 5 is a diagram illustrating an example sampling image from extracted sclera region.

FIG. 5 is a diagram illustrating an example sampling image from extracted sclera region. The example image is generally referred to by the reference number 500 and can be implemented in the computing device 700 below. For example, the sampling image 500 can be generated using the camera 108 of the system 100 of FIG. 1, the camera 726 of the computing device 700 of FIG. 7 below, and used by the image receiver 806 of the computer readable media 800 of FIG. 8 below.

FIG. 5 shows an example sampling image 500 including a portion of a sclera region having a number of blood vessels 308. In some examples, a blood vessel density score may be calculated for the sampling image 500 and averaged with blood vessel density scores calculated for a predetermined number of other sampling images of the sclera region. The resulting average blood vessel density score may be compared to a blood vessel density score threshold to predict an eye fatigue, as described herein.

The diagram of FIG. 5 is not intended to indicate that the example sampling image 500 is to include all of the components shown in FIG. 5. Rather, the example sampling image 500 can be implemented using fewer or additional components not illustrated in FIG. 5 (e.g., additional eyes, sclera, blood vessels, etc.).

Figure 6:
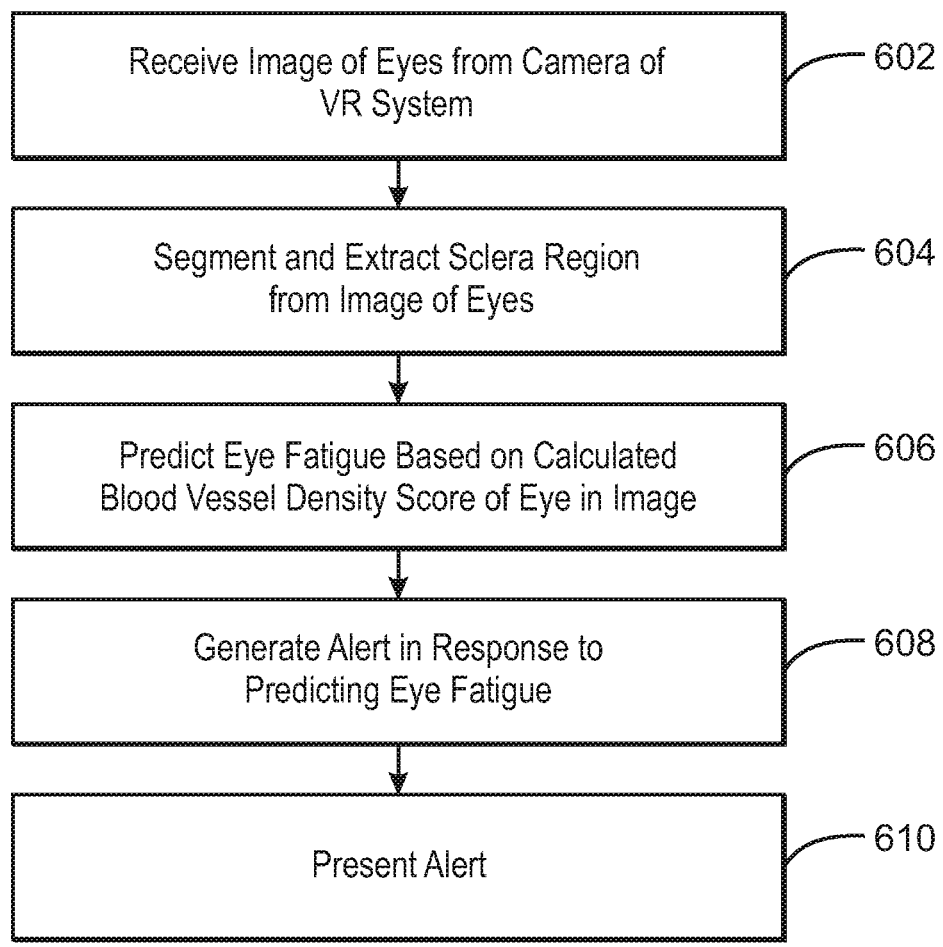
FIG. 6 is a flow chart illustrating a method for predicting eye fatigue.

FIG. 6 is a flow chart illustrating a method for predicting eye fatigue. The example method is generally referred to by the reference number 600 and can be implemented in the system 100 of FIG. 1 above, the processor 702 of the computing device 700 of FIG. 7 below, or the computer readable media 800 of FIG. 8 below.

At block 602, a processor receives one or more images of eyes from a camera of a virtual reality (VR) system. For example, the processor may receive images of the eyes at one or more predetermined intervals.

At block 604, the processor segments and extracts a sclera region from the image of the eyes. For example, the processor can segment the image of the eyes into a sclera region and a background region based on curve lines of an eyelid and an iris of the eye.

At block 606, the processor predicts an eye fatigue based on a calculated blood vessel density score of the eye in the image. In some examples, the processor may calculate the blood vessel density score on sample images from the sclera region. For example, the blood vessel density score may be an average blood vessel density score calculated for a plurality of sample images sampled from an extracted sclera region of the image. In some examples, the processor may calculate an average blood vessel density score based on a preset baseline score for a user. For example, the processor may calculate the average blood vessel density score using Eq. 1 above. In some examples, the processor may predict an eye fatigue in response to detecting that the blood vessel density score exceeds a blood vessel density score threshold. For example, the blood vessel density score threshold may be based on a preset baseline score for a user and a predetermined difference from the baseline score. In some examples, the blood vessel density score may be based on a present baseline score that is calculated during a profile creation and adjusted automatically over time. For example, the blood vessel density score may be calculated using Eq. 1 above.

At block 608, the processor generates an alert in response to predicting the eye fatigue. For example, the alert may be an audible alert, a visual alert, or a haptic alert.

At block 610, the processor presents the alert. For example, the alert may be presented as a visual alert via a display of a VR device. In some examples, the alert may be presented via an audible warning via one or more speakers of a VR device. In some examples, the alert may be present via haptic feedback on a controller of the VR device.

This process flow diagram is not intended to indicate that the blocks of the example process 600 are to be executed in any particular order, or that all of the blocks are to be included in every case. Further, any number of additional blocks not shown may be included within the example process 600, depending on the details of the specific implementation. For example, if no eye fatigue is predicted at block 606, then the method may continue back at block 602. The eye fatigue may then be predicted based on one or more of the additional images.

Figure 7:
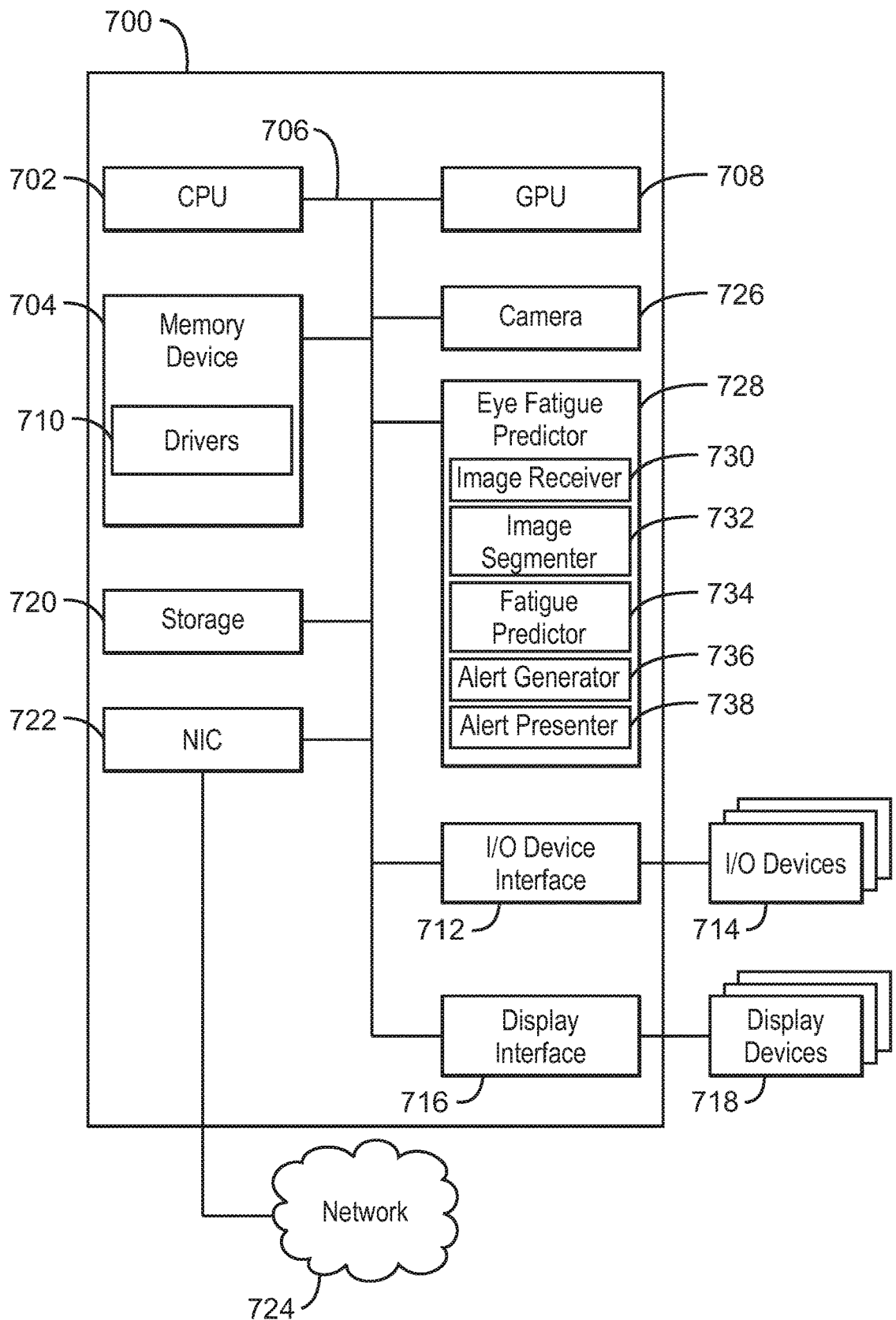
FIG. 7 is block diagram illustrating an example computing device that can predict eye fatigue.

Referring now to FIG. 7, a block diagram is shown illustrating an example computing device that can predict eye fatigue. The computing device 700 may be, for example, a laptop computer, desktop computer, tablet computer, mobile device, or wearable device, among others. In some examples, the computing device 700 may be a virtual reality (VR) system. The computing device 700 may include a central processing unit (CPU) 702 that is configured to execute stored instructions, as well as a memory device 704 that stores instructions that are executable by the CPU 702. The CPU 702 may be coupled to the memory device 704 by a bus 706. Additionally, the CPU 702 can be a single core processor, a multi-core processor, a computing cluster, or any number of other configurations. Furthermore, the computing device 700 may include more than one CPU 702. In some examples, the CPU 702 may be a system-on-chip (SoC) with a multi-core processor architecture. In some examples, the CPU 702 can be a specialized digital signal processor (DSP) used for image processing. The memory device 704 can include random access memory (RAM), read only memory (ROM), flash memory, or any other suitable memory systems. For example, the memory device 704 may include dynamic random access memory (DRAM).

The memory device 704 can include random access memory (RAM), read only memory (ROM), flash memory, or any other suitable memory systems. For example, the memory device 704 may include dynamic random access memory (DRAM).

The computing device 700 may also include a graphics processing unit (GPU) 708. As shown, the CPU 702 may be coupled through the bus 706 to the GPU 708. The GPU 708 may be configured to perform any number of graphics operations within the computing device 700. For example, the GPU 708 may be configured to render or manipulate graphics images, graphics frames, videos, or the like, to be displayed to a user of the computing device 700.

The memory device 704 can include random access memory (RAM), read only memory (ROM), flash memory, or any other suitable memory systems. For example, the memory device 704 may include dynamic random access memory (DRAM). The memory device 704 may include device drivers 710 that are configured to execute the instructions for generating eye fatigue alerts. The device drivers 710 may be software, an application program, application code, or the like.

The CPU 702 may also be connected through the bus 706 to an input/output (I/O) device interface 712 configured to connect the computing device 700 to one or more I/O devices 714. The I/O devices 714 may include, for example, a keyboard and a pointing device, wherein the pointing device may include a touchpad or a touchscreen, among others. The I/O devices 714 may be built-in components of the computing device 700, or may be devices that are externally connected to the computing device 700. In some examples, the memory 704 may be communicatively coupled to I/O devices 714 through direct memory access (DMA).

The CPU 702 may also be linked through the bus 706 to a display interface 716 configured to connect the computing device 700 to a display device 718. The display device 718 may include a display screen that is a built-in component of the computing device 700. The display device 718 may also include a computer monitor, television, or projector, among others, that is internal to or externally connected to the computing device 700.

The computing device 700 also includes a storage device 720. The storage device 720 is a physical memory such as a hard drive, an optical drive, a thumbdrive, an array of drives, a solid-state drive, or any combinations thereof. The storage device 720 may also include remote storage drives.

The computing device 700 may also include a network interface controller (NIC) 722. The NIC 722 may be configured to connect the computing device 700 through the bus 706 to a network 724. The network 724 may be a wide area network (WAN), local area network (LAN), or the Internet, among others. In some examples, the device may communicate with other devices through a wireless technology. For example, the device may communicate with other devices via a wireless local area network connection. In some examples, the device may connect and communicate with other devices via Bluetooth® or similar technology.

The computing device 700 further includes a camera 726. For example, the camera may include one or more image sensors. The camera 726 may capture images of one or more eyes of a user at predefined intervals. In some examples, the camera may include a processor to extract sclera regions and predict eye fatigue. For example, the camera 726 may include functionality such described with respect to the eye fatigue predictor 728 below. In some examples, the camera may be part of a virtual reality system including the camera 728 to capture images of one or more eyes of a user.

The computing device 700 further includes an eye fatigue predictor 728. For example, the eye fatigue predictor 728 can be used to predict eye fatigue in users of the computing device 700. The eye fatigue predictor 728 can include an image receiver 730, an image segmenter 732, a fatigue predictor 734, an alert generator 736, and an alert presenter 738. In some examples, each of the components 730-738 of the eye fatigue predictor 728 may be a microcontroller, embedded processor, or software module. The image receiver 730 can receive an image of an eye. For example, the image may be one of a plurality of images received at predefined intervals. The images may be received from the camera 726. The image segmenter 732 can segment the image into a sclera and a background based on curve lines of an eyelid and an iris of the eye. The fatigue predictor 734 can predict eye fatigue in the eye based on a calculated blood vessel density score of the eye in the image. For example, the fatigue predictor 734 can calculate the blood vessel density score based on a detected sclera of the eye in the image. The blood vessel density score may be an average of individual blood vessel density scores calculated for each of the plurality of images. For example, the blood vessel density score may be an average blood vessel density score of sample images that are subsets of a sclera region of the eye in the image. In some examples, the fatigue predictor 734 can predict eye fatigue in response to detecting the blood vessel density score in a sclera of the image exceeds a threshold density above a preset baseline score. In some examples, the blood vessel density score may be based on a present baseline score that is calculated during a profile creation and adjusted automatically over time. In some examples, the fatigue predictor 734 can calculate an average blood vessel density score based on a preset baseline score for a user. The alert generator 736 can generate an alert in response to predicting the eye fatigue. In some examples, the alert presenter 738 may present the generated alert. For example, the alert presenter 738 may present the alert as an audible warning via one or more speakers of a virtual reality (VR) device. In some examples, the alert presenter 738 may present the alert as a visual alert via a display of a virtual reality (VR) device.

The block diagram of FIG. 7 is not intended to indicate that the computing device 700 is to include all of the components shown in FIG. 7. Rather, the computing device 700 can include fewer or additional components not illustrated in FIG. 7, such as additional buffers, additional processors, and the like. The computing device 700 may include any number of additional components not shown in FIG. 7, depending on the details of the specific implementation. Furthermore, any of the functionalities of the image receiver 730, the image segmenter 732, the fatigue predictor 734, the alert generator 736, and the alert presenter 738, may be partially, or entirely, implemented in hardware and/or in the processor 702. For example, the functionality may be implemented with an application specific integrated circuit (ASIC), a field-programmable gate array (FPGA), or any other configurable circuit, or in logic implemented in the processor 702, or in any other device. In addition, any of the functionalities of the CPU 702 may be partially, or entirely, implemented in hardware and/or in a processor. The functionality of the eye fatigue predictor 728 may be implemented with an ASIC, FPGA, configurable circuit, in logic implemented in a processor, in logic implemented in a specialized graphics processing unit such as the GPU 708, or in any other device.

Figure 8:
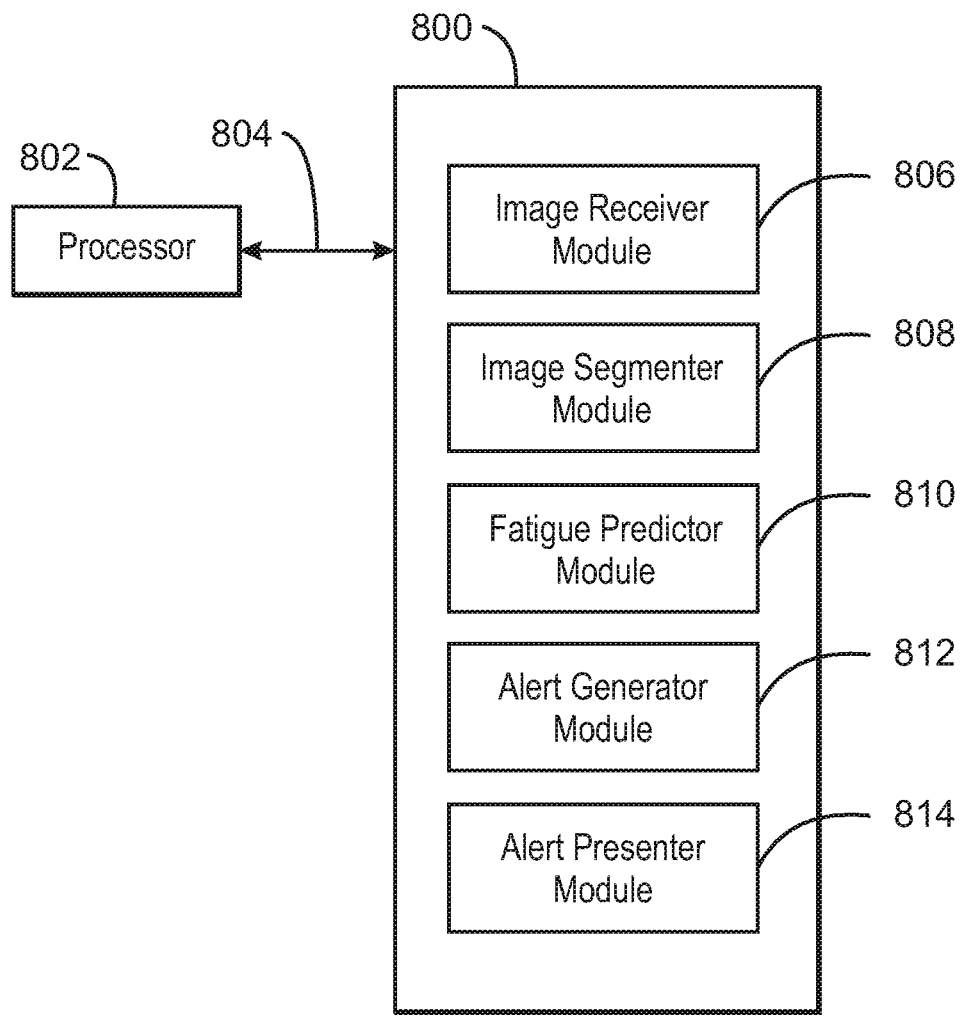
FIG. 8 is a block diagram showing computer readable media that store code for predicting eye fatigue.

FIG. 8 is a block diagram showing computer readable media 800 that store code for predicting eye fatigue. The computer readable media 800 may be accessed by a processor 802 over a computer bus 804. Furthermore, the computer readable medium 800 may include code configured to direct the processor 802 to perform the methods described herein. In some embodiments, the computer readable media 800 may be non-transitory computer readable media. In some examples, the computer readable media 800 may be storage media.

The various software components discussed herein may be stored on one or more computer readable media 800, as indicated in FIG. 8. For example, an image receiver module 806 may be configured to receive an image of eyes from a camera of a virtual reality system. In some examples, the image receiver module 806 may be configured to receiving additional images of the eyes at predetermined intervals. An image segmenter module 808 may be configured to segment and extract a sclera region from the image of the eyes, and calculate the blood vessel density score on sample images from the sclera region. In some examples, the image segmenter module 808 may be configured to segment the image of the eyes into a sclera region and a background region based on curve lines of an eyelid and an iris of the eye. A fatigue predictor module 810 may be configured to predict an eye fatigue based on a calculated blood vessel density score of the eye in the image. For example, the fatigue predictor 810 may be configured to calculate an average blood vessel density score for a plurality of sample images sampled from an extracted sclera region of the image. In some examples, the fatigue predictor module 810 may be configured to detect that the blood vessel density score exceeds a blood vessel density score threshold. In some examples, the blood vessel density score may be based on a present baseline score that is calculated during a profile creation and adjusted automatically over time. In some examples, the fatigue predictor module 810 may be configured to predict the eye fatigue based on one or more of the additional images. For example, the eye fatigue module 810 may be configured to analyze additional images until an eye fatigue is predicted. An alert generator module 812 may be configured to generate an alert in response to predicting the eye fatigue. An alert presenter module 814 may be configured to present the alert within the VR system. For example, the alert presenter module 814 may be configured to present the alert as an audible warning via one or more speakers of a virtual reality (VR) device. In some examples, the alert presenter module 814 may be configured to present the alert as a visual alert via a display of a virtual reality (VR) device.

The block diagram of FIG. 8 is not intended to indicate that the computer readable media 800 is to include all of the components shown in FIG. 8. Further, the computer readable media 800 may include any number of additional components not shown in FIG. 8, depending on the details of the specific implementation.

Examples

Example 1 is an apparatus for predicting eye fatigue. The apparatus includes an image receiver to receive an image of an eye. The apparatus includes a fatigue predictor to predict eye fatigue in the eye based on a calculated blood vessel density score of the eye in the image. The apparatus includes an alert generator to generate an alert in response to predicting the eye fatigue.

Example 2 includes the apparatus of example 1, including or excluding optional features. In this example, the apparatus includes an image segmenter to segment the image into a sclera and a background based on curve lines of an eyelid and an iris of the eye.

Example 3 includes the apparatus of any one of examples 1 to 2, including or excluding optional features. In this example, the fatigue predictor is to calculate the blood vessel density score based on a detected sclera of the eye in the image.

Example 4 includes the apparatus of any one of examples 1 to 3, including or excluding optional features. In this example, the fatigue predictor is to predict eye fatigue in response to detecting the blood vessel density score in a sclera of the image exceeds a threshold density above a preset baseline score.

Example 5 includes the apparatus of any one of examples 1 to 4, including or excluding optional features. In this example, the blood vessel density score is based on a present baseline score that is calculated during a profile creation and adjusted automatically over time.

Example 6 includes the apparatus of any one of examples 1 to 5, including or excluding optional features. In this example, the image comprises one of a plurality of images received at predefined intervals. The blood vessel density score includes an average of individual blood vessel density scores calculated for each of the plurality of images.

Example 7 includes the apparatus of any one of examples 1 to 6, including or excluding optional features. In this example, the blood vessel density score comprises an average blood vessel density score of sample images including subsets of a sclera region of the eye in the image.

Example 8 includes the apparatus of any one of examples 1 to 7, including or excluding optional features. In this example, the fatigue predictor is to calculate an average blood vessel density score based on a preset baseline score for a user.

Example 9 includes the apparatus of any one of examples 1 to 8, including or excluding optional features. In this example, the apparatus includes an alert presenter to present the generated alert.

Example 10 includes the apparatus of any one of examples 1 to 9, including or excluding optional features. In this example, the apparatus is a virtual reality system including a camera to capture the image of the eye.

Example 11 is a method for predicting eye fatigue. The method includes receiving, via a processor, an image of eyes from a camera of a virtual reality system. The method also includes predicting, via the processor, an eye fatigue based on a calculated blood vessel density score of the eye in the image. The method further includes and generating, via the processor, an alert in response to predicting the eye fatigue.

Example 12 includes the method of example 11, including or excluding optional features. In this example, the method includes presenting, via the processor, the alert within the VR system.

Example 13 includes the method of any one of examples 11 to 12, including or excluding optional features. In this example, the method includes segmenting and extracting a sclera region from the image of the eyes, and calculating the blood vessel density score on sample images from the sclera region.

Example 14 includes the method of any one of examples 11 to 13, including or excluding optional features. In this example, the method includes segmenting the image of the eyes into a sclera region and a background region based on curve lines of an eyelid and an iris of the eye.

Example 15 includes the method of any one of examples 11 to 14, including or excluding optional features. In this example, the blood vessel density score includes an average blood vessel density score calculated for a plurality of sample images sampled from an extracted sclera region of the image.

Example 16 includes the method of any one of examples 11 to 15, including or excluding optional features. In this example, predicting the eye fatigue includes detecting that the blood vessel density score exceeds a blood vessel density score threshold.

Example 17 includes the method of any one of examples 11 to 16, including or excluding optional features. In this example, the blood vessel density score is based on a present baseline score that is calculated during a profile creation and adjusted automatically over time.

Example 18 includes the method of any one of examples 11 to 17, including or excluding optional features. In this example, the method includes receiving additional images of the eyes at predetermined intervals. The eye fatigue is predicted based on one or more of the additional images.

Example 19 includes the method of any one of examples 11 to 18, including or excluding optional features. In this example, the alert is presented as an audible warning via one or more speakers of a virtual reality (VR) device.

Example 20 includes the method of any one of examples 11 to 19, including or excluding optional features. In this example, the alert is presented as a visual alert via a display of a virtual reality (VR) device.

Example 21 is at least one computer readable medium for predicting eye fatigue having instructions stored therein that. The computer-readable medium includes instructions that direct the processor to receive an image of eyes from a camera of a virtual reality system. The computer-readable medium includes instructions that direct the processor to predict an eye fatigue based on a calculated blood vessel density score of the eye in the image. The computer-readable medium includes instructions that direct the processor to generate an alert in response to predicting the eye fatigue.

Example 22 includes the computer-readable medium of example 21, including or excluding optional features. In this example, the computer-readable medium includes instructions to present the alert within the VR system.

Example 23 includes the computer-readable medium of any one of examples 21 to 22, including or excluding optional features. In this example, the computer-readable medium includes instructions to segment and extract a sclera region from the image of the eyes, and calculate the blood vessel density score on sample images from the sclera region.

Example 24 includes the computer-readable medium of any one of examples 21 to 23, including or excluding optional features. In this example, the computer-readable medium includes instructions to segment the image of the eyes into a sclera region and a background region based on curve lines of an eyelid and an iris of the eye.

Example 25 includes the computer-readable medium of any one of examples 21 to 24, including or excluding optional features. In this example, the computer-readable medium includes instructions to calculate an average blood vessel density score for a plurality of sample images sampled from an extracted sclera region of the image.

Example 26 includes the computer-readable medium of any one of examples 21 to 25, including or excluding optional features. In this example, the computer-readable medium includes instructions to detect that the blood vessel density score exceeds a blood vessel density score threshold.

Example 27 includes the computer-readable medium of any one of examples 21 to 26, including or excluding optional features. In this example, the computer-readable medium includes instructions to calculate a present baseline score that is during a profile creation and adjust the present baseline score automatically over time. The blood vessel density score is based on the present baseline score.

Example 28 includes the computer-readable medium of any one of examples 21 to 27, including or excluding optional features. In this example, the computer-readable medium includes instructions to receive additional images of the eyes at predetermined intervals. The eye fatigue is predicted based on one or more of the additional images.

Example 29 includes the computer-readable medium of any one of examples 21 to 28, including or excluding optional features. In this example, the computer-readable medium includes instructions to present the alert as an audible warning via one or more speakers of a virtual reality (VR) device.

Example 30 includes the computer-readable medium of any one of examples 21 to 29, including or excluding optional features. In this example, the computer-readable medium includes instructions to present the alert as a visual alert via a display of a virtual reality (VR) device.

Example 31 is a system for predicting eye fatigue. The system includes an image receiver to receive an image of an eye. The system includes a fatigue predictor to predict eye fatigue in the eye based on a calculated blood vessel density score of the eye in the image. The system includes an alert generator to generate an alert in response to predicting the eye fatigue.

Example 32 includes the system of example 31, including or excluding optional features. In this example, the system includes an image segmenter to segment the image into a sclera and a background based on curve lines of an eyelid and an iris of the eye.

Example 33 includes the system of any one of examples 31 to 32, including or excluding optional features. In this example, the fatigue predictor is to calculate the blood vessel density score based on a detected sclera of the eye in the image.

Example 34 includes the system of any one of examples 31 to 33, including or excluding optional features. In this example, the fatigue predictor is to predict eye fatigue in response to detecting the blood vessel density score in a sclera of the image exceeds a threshold density above a preset baseline score.

Example 35 includes the system of any one of examples 31 to 34, including or excluding optional features. In this example, the blood vessel density score is based on a present baseline score that is calculated during a profile creation and adjusted automatically over time.

Example 36 includes the system of any one of examples 31 to 35, including or excluding optional features. In this example, the image is one of a plurality of images received at predefined intervals. The blood vessel density score is an average of individual blood vessel density scores calculated for each of the plurality of images.

Example 37 includes the system of any one of examples 31 to 36, including or excluding optional features. In this example, the blood vessel density score is an average blood vessel density score of sample images comprising subsets of a sclera region of the eye in the image.

Example 38 includes the system of any one of examples 31 to 37, including or excluding optional features. In this example, the fatigue predictor is to calculate an average blood vessel density score based on a preset baseline score for a user.

Example 39 includes the system of any one of examples 31 to 38, including or excluding optional features. In this example, the system includes an alert presenter to present the generated alert.

Example 40 includes the system of any one of examples 31 to 39, including or excluding optional features. In this example, the system is a virtual reality system including a camera to capture the image of the eye.

Example 41 is a system for predicting eye fatigue. The system includes means for receiving an image of an eye. The system also includes means for predicting eye fatigue in the eye based on a calculated blood vessel density score of the eye in the image. The system further includes means for generating an alert in response to predicting the eye fatigue.

Example 42 includes the system of example 41, including or excluding optional features. In this example, the system includes means for segmenting the image into a sclera and a background based on curve lines of an eyelid and an iris of the eye.

Example 43 includes the system of any one of examples 41 to 42, including or excluding optional features. In this example, the means for predicting eye fatigue is to calculate the blood vessel density score based on a detected sclera of the eye in the image.

Example 44 includes the system of any one of examples 41 to 43, including or excluding optional features. In this example, the means for predicting eye fatigue is to predict eye fatigue in response to detecting the blood vessel density score in a sclera of the image exceeds a threshold density above a preset baseline score.

Example 45 includes the system of any one of examples 41 to 44, including or excluding optional features. In this example, the blood vessel density score is based on a present baseline score that is calculated during a profile creation and adjusted automatically over time.

Example 46 includes the system of any one of examples 41 to 45, including or excluding optional features. In this example, the image is one of a plurality of images received at predefined intervals. The blood vessel density score is an average of individual blood vessel density scores calculated for each of the plurality of images.

Example 47 includes the system of any one of examples 41 to 46, including or excluding optional features. In this example, the blood vessel density score is an average blood vessel density score of sample images including subsets of a sclera region of the eye in the image.

Example 48 includes the system of any one of examples 41 to 47, including or excluding optional features. In this example, the means for predicting eye fatigue is to calculate an average blood vessel density score based on a preset baseline score for a user.

Example 49 includes the system of any one of examples 41 to 48, including or excluding optional features. In this example, the system includes means for presenting the generated alert.

Example 50 includes the system of any one of examples 41 to 49, including or excluding optional features. In this example, the system includes means for capturing the image of the eye.

Not all components, features, structures, characteristics, etc. described and illustrated herein need be included in a particular aspect or aspects. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some aspects have been described in reference to particular implementations, other implementations are possible according to some aspects. Additionally, the arrangement and/or order of circuit elements or other features illustrated in the drawings and/or described herein need not be arranged in the particular way illustrated and described. Many other arrangements are possible according to some aspects.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more aspects. For instance, all optional features of the computing device described above may also be implemented with respect to either of the methods or the computer-readable medium described herein. Furthermore, although flow diagrams and/or state diagrams may have been used herein to describe aspects, the techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

What is claimed is:

1. An apparatus comprising:
    at least one memory;
    machine readable instructions; and
    programmable circuitry to at least one of instantiate or execute the machine readable instructions to:
        identify a first curved line in an image of an eye corresponding to an eye lid;
        identify a second curved line in the image of the eye corresponding to an iris;
        identify a sclera based on the first curved line and the second curved line;
        calculate a blood vessel density score based on blood vessels in the sclera; and
        predict eye fatigue based on the blood vessel density score.

2. The apparatus of claim 1, wherein the image is a plurality of images, and the blood density score is an average for the plurality of images.

3. The apparatus of claim 1, wherein the sclera in the image is segmented into subsets, and the blood density score is an average for the subsets.

4. The apparatus of claim 1, wherein the programmable circuitry is to:
    compare the blood density score to a threshold blood density score; and
    predict the eye fatigue when the blood density score satisfies the threshold blood density score.

5. The apparatus of claim 1, wherein the programmable circuitry is to generate an alert when eye fatigue is predicted.

6. The apparatus of claim 5, wherein the alert is a visual alert.

7. The apparatus of claim 5, wherein the alert is an audio alert.

8. The apparatus of claim 5, wherein the alert is a haptic alert.

9. An apparatus comprising:
    a virtual reality display;
    at least one memory;
    machine readable instructions; and
    programmable circuitry to at least one of instantiate or execute the machine readable instructions to:
        identify a sclera in a first image of an eye;
        identify the sclera in a second image of the eye, the second image taken before the first image during use of the virtual reality display;
        calculate a blood vessel density score based on blood vessels in the sclera;
        calculate a threshold blood vessel density score based on blood vessels in the sclera in the second image;
        compare the blood density score to the threshold blood density score; and
        predict eye fatigue when the blood density score satisfies the threshold blood density score.

10. The apparatus of claim 9, further including a camera to capture the first image and the second image.

11. An article of manufacture comprising instructions to cause programmable circuitry to at least:
    identify a first curved line in an image of an eye corresponding to an eye lid;
    identify a second curved line in the image of the eye corresponding to an iris;
    identify a sclera based on the first curved line and the second curved line;
    identify blood vessels in the sclera;
    calculate a blood vessel density score based on the blood vessels in the sclera; and
    predict eye fatigue based on the blood vessel density score.

12. The article of manufacture of claim 11 wherein the image is a plurality of images, and the blood density score is an average for the plurality of images.

13. The article of manufacture of claim 11 wherein the sclera in the image is segmented into subsets, and the blood density score is an average for the subsets.

14. The article of manufacture of claim 11 wherein the instructions cause the programmable circuitry to:
    compare the blood density score to a threshold blood density score; and
    predict the eye fatigue when the blood density score satisfies the threshold blood density score.

15. The article of manufacture of claim 11 wherein the instructions cause the programmable circuitry to generate an alert when eye fatigue is predicted.

16. An article of manufacture comprising instructions to cause programmable circuitry to at least:
    identify blood vessels in a sclera in a first image of an eye;
    identify the sclera in a second image of the eye, the second image taken before the first image;
    calculate a blood vessel density score based on the blood vessels in the sclera;
    calculate a threshold blood vessel density score based on blood vessels in the sclera in the second image;
    compare the blood density score to the threshold blood density score; and
    predict eye fatigue when the blood density score satisfies the threshold blood density score.

* * * * *